(12) United States Patent
Stewart et al.

(10) Patent No.: US 6,548,053 B1
(45) Date of Patent: Apr. 15, 2003

(54) CONTROL OF INTRA-OCULAR PRESSURE

(75) Inventors: Paul Michael Stewart, West Midlands (GB); Philip Ian Murray, Birmingham (GB)

(73) Assignee: The University of Birmingham, Birmingham (GB)

( * ) Notice: Subject to any disclaimer, the term of this patent is extended or adjusted under 35 U.S.C. 154(b) by 0 days.

(21) Appl. No.: 09/591,406

(22) Filed: Jun. 12, 2000

(30) Foreign Application Priority Data

Jun. 24, 1999 (GB) .............................................. 9914648

(51) Int. Cl.$^7$ ............................. A61K 9/08; A61K 9/06; A61K 9/00
(52) U.S. Cl. ................................ 424/78.04; 424/78.02; 424/400; 424/422; 424/427
(58) Field of Search .............................. 424/427, 78.04, 424/400, 422, 78.02

(56) References Cited

U.S. PATENT DOCUMENTS

| 3,070,623 A | * 12/1962 | Gottfried et al. | ............ 424/422 |
| 4,863,912 A | * 9/1989 | Southren et al. | ............ 514/177 |
| 5,474,985 A | * 12/1995 | Polansky et al. | ............ 514/26 |

FOREIGN PATENT DOCUMENTS

| WO | WO-90/04399 A1 | * 5/1990 |
| WO | WO-97/07789 A1 | * 3/1997 |

* cited by examiner

*Primary Examiner*—Thurman K. Page
*Assistant Examiner*—Rachel M. Bennett
(74) *Attorney, Agent, or Firm*—Ohlandt, Greeley, Ruggiero & Perle, L.L.P.

(57) ABSTRACT

A method of reducing intra-ocular pressure (IOP) in a patient afflicted with elevated IOP is disclosed. The method comprises the step of administering (preferably topically to an afflicted eye) to the patient a therapeutically effective amount of a $\beta$-HSD-1 inhibitor.

10 Claims, 2 Drawing Sheets

CONTROL OF INTRA-OCULAR PRESSURE

The present invention is concerned with the regulation of intra-ocular pressure (IOP), and is more particularly concerned with the reduction of elevated IOP.

The ion transport mechanisms underlying fluid balance within the eye and the maintenance of intra-ocular pressure (IOP) are poorly understood. Aqueous humour (abbreviated to aqueous hereinafter) is produced by the ciliary epithelium, a complex bi-layer consisting of an inner non-pigmented epithelial layer in direct contact with the aqueous and an outer pigmented epithelial layer adjacent to the highly vascularised connective tissue stroma of the ciliary processes. Aqueous circulates from the posterior chamber into the anterior chamber and is drained predominantly through the trabecular meshwork into Schlemm's canal, and to a lesser extent through the uveoscleral pathways. The production of aqueous is dependent on several mechanisms: active transport, carbonic anhydrase inhibition, diffusion and ultrafiltration. IOP is dependent upon the relative rates of formation and drainage of the aqueous.

It is known that the membrane-bound enzyme complex $Na^+/K^+$ ATPase (sodium potassium adenosine triphosphatase) in the non-pigmented ciliary epithelium has an important role in the active secretion of aqueous. In other tissues (e.g. kidney, colon and salivary gland) sodium transport is facilitated by the stimulation of $Na^+/K^+$ ATPase by adrenocorticosteroids, such as glucocorticoids (e.g. cortisol) or mineralocorticoids (e.g. aldosterone). In these tissues, corticosteroid hormone action is regulated by 11-β-hydroxysteroid dehydrogenase (11-β-HSD). Two isoforms of the enzyme are known: 11-β-HSD1, a NADP(H)-dependent enzyme acting primarily as an oxo-reductase in vivo (catalysing the conversion of inactive cortisone to hormonally active cortisol, and references hereinafter to a β-HSD-1 inhibitor are intended to relate to the inhibition of this oxo-reductase activity), and 11-β-HSD2, a high affinity NAD-dependent dehydrogenase (catalysing the conversion of cortisol to hormonally inactive cortisone). In the kidney, sodium transport is predominantly regulated by 11-β-HSD2, as demonstrated by the ingestion of carbenoxolone (a potent 11-β-HSD1 and 11-β-HSD2 inhibitor) which results in increased levels of cortisol and cortisol-mediated renal sodium retention.

It is also known that the eye is an important target tissue for corticosteroids. Both mineralocorticoid receptors (MR) and glucocorticoid receptors (GR) have been demonstrated in the eye, as well as a number of steroid hormones within the aqueous (including cortisol and aldosterone). Corticosteroids are implicated in the natural diurnal variation of IOP. The variation is attributable to changes in the rate of aqueous formation which varies synchronously with endogenous circulating cortisol and catecholamines. Glucocorticoids also cause an increase in IOP secondary to a decrease in the facility of aqueous outflow (corticosteroid-induced glaucoma). The majority of such cases are secondary to exogenous use of corticosteroids (systemic, topical or periocular), but some cases arise from abnormal endogenous corticosteroid production (e.g. Cushings syndrome).

However, little is known about the role of corticosteroids in the regulation of aqueous production.

It is an object of the present invention in at least one aspect, to provide a medicament capable of lowering intra-ocular pressure.

In a first aspect, the present invention resides in the use of a β-HSD-1 inhibitor for the manufacture of a pharmaceutical composition for lowering intra-ocular pressure.

According to a second aspect of the present invention, there is provided a pharmaceutical composition suitable for topical administration to an eye, said composition comprising a β-HSD-1 inhibitor and a pharmaceutically acceptable diluent or carrier suitable for administration to the eye.

According to a third aspect of the present invention, there is provided a method of reducing intra-ocular pressure (IOP) in a patient afflicted with elevated IOP, comprising the step of administering (preferably topically to an afflicted eye) to the patient a therapeutically effective amount of a β-HSD-1 inhibitor.

The various aspects of the present invention are based on the discovery by the Inventor that 11-β-HSD1 and 11-β-HSD2 are present in the eye, and that surprisingly 11-β-HSD1 has a much higher activity in the eye than 11-β-HSD2, such that $Na^+/K^+$ ATPase-moderated aqueous production is primarily regulated by 11-β-HSD1 rather than 11-β-HSD2. This is contrary to what would have been expected from other target tissues. Said elevated IOP may be as a result of exogenous corticosteroid administration, or as a result of disease (e.g. glaucoma and Cushing's syndrome), although it will be understood that the actual cause of elevated IOP is immaterial to the effectiveness of the invention.

Said β-HSD-1 inhibitor may be provided by liquorice or a derivative thereof (e.g. glycyrrhetinic acid or carbenoxolone). Alternatively, said β-HSD-1 inhibitor may be progesterone or a derivative thereof (e.g. 11α-hydroxy or 11β-hydroxy progesterone). Preferably, said β-HSD-1 inhibitor is carbenoxolone. It will be understood that said 11-β-HSD1 inhibitor may also be an 11-β-HSD2 inhibitor.

An embodiment of the present invention will now be described with reference to the accompanying drawings in which.

Figure 1:
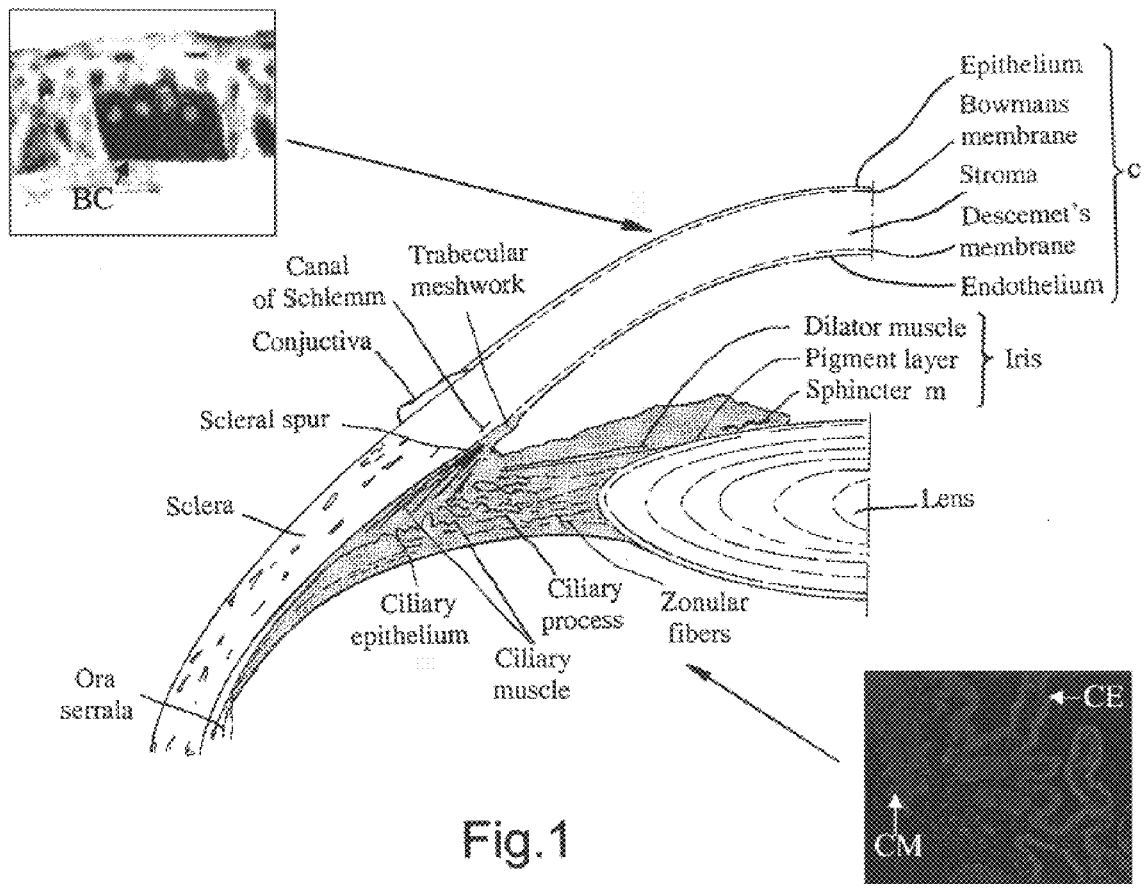
FIG. 1 shows the immunolocalisation of 11β-HSD1 in ocular tissues.

Referring to FIG. 1, localisation of 11β-HSD1 and 11β-HSD2 was investigated using immunohistochemical techniques. Analyses were performed using antisera raised in sheep against human 11β-HSD1 and 11β-HSD2 on formalin-fixed, paraffin-embedded sections of human eyes. Positive staining was confirmed by comparison to sections incubated with the peptide pre-treated antisera. 11β-HSD1 immunoreactivity was demonstrated in the corneal endothelium, specific basal cells of the corneal epithelium (BC in FIG. 1), the non-pigmented ciliary epithelium and ciliary muscle (CE and CM respectively in FIG. 1) and the sphincter and dilator muscles of the iris.

Figure 2:
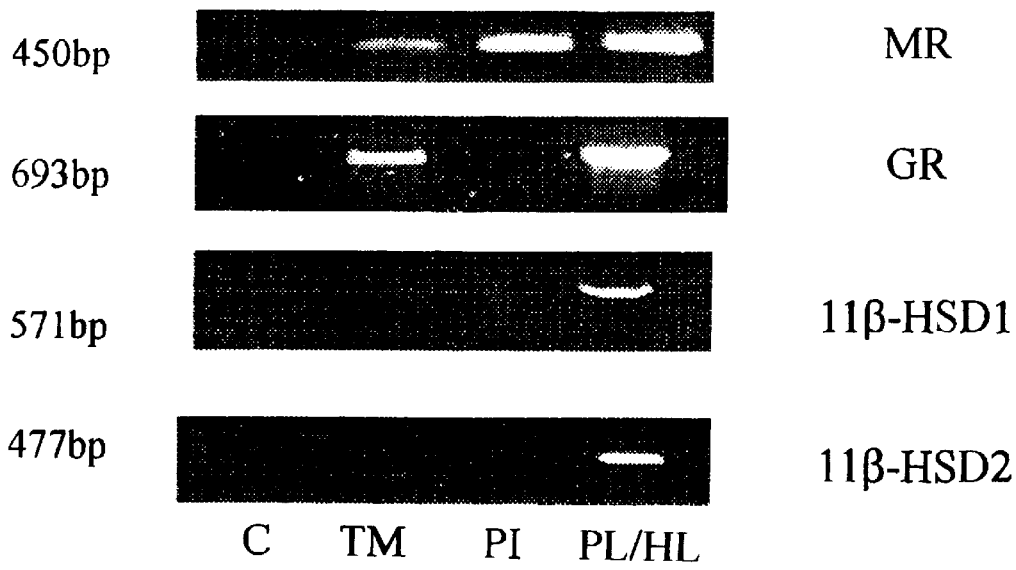
FIG. 2 shows sections from an electrophoresis gel of a human trabecular meshwork specimen.

Referring to FIG. 2, trabecular meshwork and peripheral iris specimens were obtained from 21 consecutive patients undergoing glaucoma filtration surgery. The specimens were snap frozen in liquid nitrogen and stored at −70° C. until further analysis. The presence of trabecular meshwork was confirmed by formalin fixing and paraffin wax embedding three of the specimens, followed by sectioning and staining with haematoxilin and eosin. The corresponding iris specimens were treated in a similar manner. RNA was extracted from the remaining 18 pairs of specimens and analysed by reverse transcription PCR for the presence of 11β-HSD1, 11β-HSD2, MR and GR (using 18S RNA as an internal standard). The conditions used for the RT-PCR were as follows:

```
11β-HSD1 primers:
    5'-CTC-GAG-TCG-GAT-GGC-TTT-TAT-G-3'   (sense)
    5'-ACT-TGC-TTG-CAG-AAT-AGG-3'         (antisense)
product size       571bp
cycle conditions   95° C. 5 min     1 cycle
                   95° C. 1 min}
                   50° C. 1 min}    35 cycles
                   72° C. 1 min}
                   72° C. 5 min     1 cycle 11β-HSD2 primers:
    5'-ACC-GTA-TTG-GAG-TTG-AAC-AGC-3'     (sense)
    5'-TCA-CTG-ACT-CTG-TCT-TGA-AGC-3'     (antisense)
product size       477bp
cycle conditions   95° C. 5 min     1 cycle
                   95° C. 1 min}
                   47° C. 1 min}    35 cycles
                   72° C. 1 min}
                   72° C. 5 min     1 cycle MR primers:
    5'-AAC-TTG-CCT-CTT-GAG-GAC-CAA-3'     (sense)
    5'-AGG-ATT-CCA-GCA-GGT-CGC-TC-3'      (antisense)
product size       450bp
cycle conditions   95° C. 5 min     1 cycle
                   95° C. 1 min}
                   55° C. 1 min}    35 cycles
                   72° C. 1 min}
                   72° C. 5 min     1 cycle GR primers:
    5'-TCG-ACC-AGT-GTT-CCA-GAG-AAC-3'     (sense)
    5'-TTT-CGG-AAC-CAA-CGG-GAA-TTG-3'     (antisense)
product size       693bp
cycle conditions   95° C. 5 min     1 cycle
                   95° C. 1 min}
                   55° C. 1 min}    35 cycles
                   72° C. 1 min}
                   72° C. 5 min     1 cycle 18S primers:
                   Quantum RNA kit, Ambion Inc., Texas, USA
product size       540 bp
cycle conditions   95° C. 5 min     1 cycle
                   95° C. 1 min}
                   50° C. 1 min}    35 cycles
                   72° C. 1 min}
                   72° C. 5 min     1 cycle
```

PCR reaction components: 50 mM KCl, 10 mM Tris-HCl (pH 9.0), 0.1% Triton X-100 (Promega) 1.5 mM $MgCl_2$, 0.2 µM each dNTP, 0.5 mM of each primer and 1 U Taq DNA polymerase (Promega).

As can be seen from FIG. 2, the trabecular meshwork (TM) samples proved positive for GR and MR. None of the samples showed evidence of either 11β-HSD isozyme. The peripheral iris samples showed the presence of GR (data not shown). In all cases, RNA derived from human liver (HL) and placenta (PL) was used as a positive control. A negative control (C) was also used.

Aqueous humour cortisol (F) and cortisone (E) concentrations were determined by gas chromatography with mass spectrometry (GC/MS) by pooling aqueous humour specimens obtained from 16 patients undergoing phacoemulsification of cataracts under peribulber anaesthesia. The specimens were collected at the start of the surgical procedure before the anterior chamber had been contaminated by viscoelastics or balanced salt solution. GC/MS of the specimens confirmed higher levels of cortisol (3.6 ng/ml) than cortisone (0.25 ng/ml), an F/E ratio of 14.4:1. This value is much higher than the urinary free ratio (see below) and the circulating ratio of about 3:1. This finding is indicative of preferential 11β-HSD1 activity within the eye.

A clinical study was undertaken to assess the functional significance of 11β-HSD within the eye by oral administration of carbenoxolone, a known inhibitor of both 11β-HSD1 and 11β-HSD2. The study was undertaken on eight healthy male volunteers who were not on any systemic or topical medications and had no family history of glaucoma. Baseline intra-ocular pressure readings were measured using the same Goldmann applanation tonometer at 08:00, 12:00, 16:00 and 20:00 hours on two consecutive days. Systolic and diastolic blood pressures were also measured at each time point. Venous blood was analysed for serum electrolytes on day one and urine was collected for 24-hour urinary free cortisol and GC/MS for cortisol/cortisone ratios. The subjects then commenced a course of 100 mg carbenoxolone taken orally three times a day for seven consecutive days. The IOP measurements and blood pressure recordings were repeated at each time point on the third and seventh day of carbenoxolone ingestion (i.e. days five and nine of the study). Urea and electrolytes were also measured on these days and inhibition of 11β-HSD was confirmed by comparing the original urinary F/E ratio with that from urine aliquoted from a further 24-hour collection performed between days six and seven of ingestion.

Figure 3:
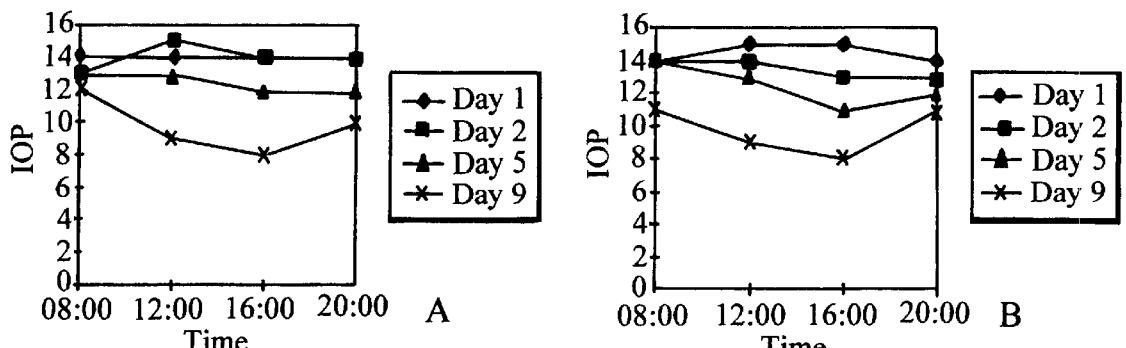
FIGS. 3 and 4 are plots of intra-ocular pressure against time for one subject and the mean for eight subject subjects receiving oral carbenoxolone respectively.

FIG. 3 shows the variation of IOP with time on days 1, 2, 5 and 9 for the right and left eye (panel A and B respectively) of one subject. It can be seen that IOP was generally lower in both eyes on day 5 (third day of carbenoxolone ingestion) than on days 1 and 2 (pre-carbenoxolone ingestion), and even lower on day 9 (seventh day of carbenoxolone ingestion).

Figure 4:
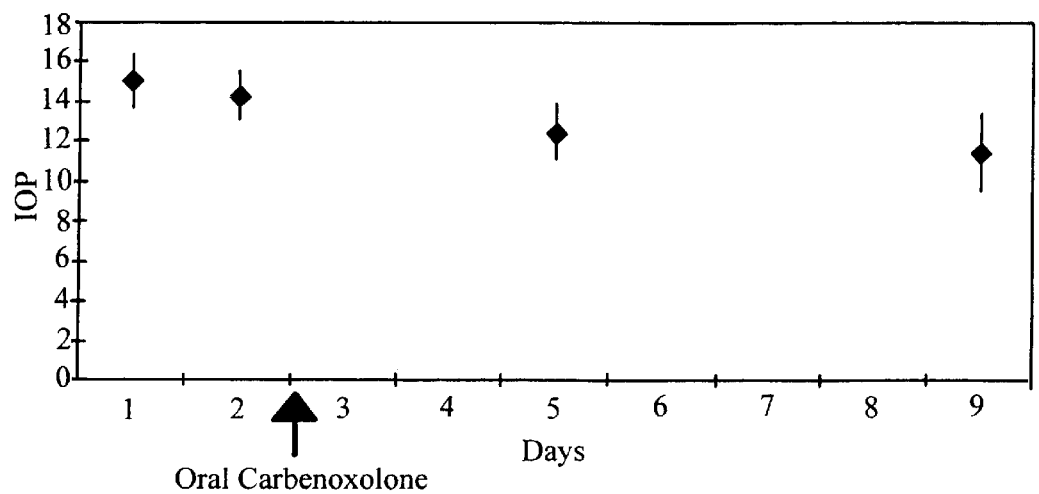

FIG. 4 shows the mean change in IOP for the eight subjects over the course of the study. There was an overall reduction in IOP by 18.2% (pre-IOP=14.7±1.39, per-IOP=12.00±1.87, p<0.000001) on ingesting carbenoxolone. All eight subjects showed a decrease in IOP, this drop being significant in seven of the individuals (<0.01). There was no difference between each eye of each subject. The IOP was lower on day seven of ingestion (11.50±2.08) than on day three (12.48±1.48) compared with the mean baseline values (p<0.0001 for both days), the difference between days three and seven being significant (p<0.001). There was also a small reduction in intra-ocular pressure during the course of the day, i.e. from 08:00 hrs to 20:00 hrs (baseline reduction of 0.38±1.16 (2.51%), p=0.076). This diurnal variation became more marked on days three and seven of ingestion (reduction of 0.86±0.83 (6.51%), p=0.0058, and 2.25±1.91 (17.31%), p=0.0006 respectively). This diurnal variation was also significantly different from baseline on day seven of ingestion (p<0.0001). Systolic and diastolic blood pressures and serum electrolytes remained stable throughout.

There was no significant change in the 24-hour urinary free cortisol, but the GC/MS determined F/E ratios increased significantly (pre-F/E=0.497±0.189, per-F/E=1.144±0.382, p=0.004) indicating inhibition of 11β-HSD. These results are indicative of inhibition of cortisone formation from cortisol (11β-HSD2 inhibition) and reflect the relative 11β-HSD1/HSD2 activities in the kidneys. In addition, there was a significant decrease in the tetrahydrocortisol (THF)+allo- THF/tetrahydrocortisone (THE) ratio (pre-THF+allo-THF/THE=0.92±0.23, per-THF+allo-THF/THE=0.7±0.19, p=0.0012). This reflects the relative 11β-HSD1/HSD2 activities predominantly in the liver.

Thus, it has been shown that 11β-HSD is present in ocular tissue, in particular the non-pigmented ciliary epithelium. The various data showing the presence of cortisol in excess of cortisone indicates preferential activity of 11β-HSD1. This is confirmed by the results of the above clinical study which show that carbenoxolone (an inhibitor of both 11β-HSD isozymes) causes a significant decrease in IOP, this being indicative of its inhibitory effect on the oxo-reductase activity of 11β-HSD1 rather than inhibition of 11β-HSD2 dehydrogenase activity. It is suggested that in the eye, under normal physiological conditions, cortisol acts as a mineralocorticoid through either the MR or GR. The membrane bound $Na^+/K^+$ ATPase in the non-pigmented ciliary epithelium is activated, thereby facilitating sodium and water transport into the posterior chamber and controlling the production of aqueous. The reduction of IOP seen with oral carbenoxolone suggests that 11β-HSD1 has a fundamental role in the maintenance of IOP, by controlling the exposure of MR and GR to aqueous cortisol.

We claim:

1. A method of reducing intra-ocular pressure (IOP) in a patient afflicted with elevated IOP, comprising administering to the patient an intra-ocular pressure lowering effective amount of a β-HSD-1 inhibitor.

2. A method in accordance with claim 1, wherein said β-HSD-1 inhibitor is administered topically to an afflicted eye of the patient.

3. A method in accordance with claim 1, wherein said β-HSD-1 inhibitor is provided by liquorice or a derivative thereof.

4. A method in accordance with claim 3, wherein said liquorice derivative is selected from the group consisting of glycyrrhetinic acid and carbenoxolone.

5. A method in accordance with claim 4, wherein said β-HSD-1 inhibitor is carbenoxolone.

6. A method in accordance with claim 1, wherein said β-HSD-1 inhibitor is progesterone or a derivative thereof.

7. A method in accordance with claim 6, wherein said progesterone derivative is selected from the group consisting of 11α-hydroxy progesterone and 11β-hydroxy progesterone.

8. A method in accordance with claim 1, wherein said 11-β-HSD1 inhibitor is also an 11-β-HSD2 inhibitor.

9. A method in accordance with claim 1, wherein said elevated IOP is as a result of exogenous corticosteroid administration.

10. A method in accordance with claim 1, wherein said elevated IOP is as a result of glaucoma or Cushing's syndrome.

* * * * *